US00PP25135P2

(12) United States Plant Patent
Wood

(10) Patent No.: US PP25,135 P2
(45) Date of Patent: Dec. 2, 2014

(54) ***HYDRANGEA* PLANT NAMED 'SMHPFL'**

(50) Latin Name: *Hydrangea paniculata*
Varietal Denomination: SMHPFL

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 13/987,719

(22) Filed: Aug. 23, 2013

(51) Int. Cl.
*A01H 5/00* (2006.01)

(52) U.S. Cl.
USPC ..... Plt./250

(58) Field of Classification Search
CPC ..... A01H 5/00
USPC ..... Plt./250
See application file for complete search history.

(56) References Cited

PUBLICATIONS

UPOV hit on CA PBR 12-7705 for *hydrangea* named 'SMHPFL' application publication date Oct. 31, 2012.*

* cited by examiner

*Primary Examiner* — Anne Grunberg
(74) *Attorney, Agent, or Firm* — C. A. Whealy

(57) ABSTRACT

A new and distinct cultivar of *Hydrangea* plant named 'SMHPFL', characterized by its upright and somewhat outwardly spreading plant habit; strong and sturdy stems; dark green-colored leaves; and large inflorescences with white-colored sterile flowers that become red with development in the autumn.

2 Drawing Sheets

Botanical designation: *Hydrangea paniculata.*
Cultivar denomination: 'SMHPFL'.

BACKGROUND OF THE INVENTION

The present invention relates to a new and distinct *Hydrangea* plant, botanically known as *Hydrangea paniculata* and hereinafter referred to by the name 'SMHPFL'.

The new *Hydrangea* plant is a product of a planned breeding program conducted by the Inventor in Grand Haven, Mich. The objective of the breeding program was to develop new *Hydrangea* plants with strong stems and large and attractive inflorescences.

The new *Hydrangea* plant originated from a cross-pollination during the spring of 2007 of *Hydrangea paniculata* 'Pink Lady M2A', not patented, as the female, or seed parent and *Hydrangea paniculata* 'Pink Lady M2B', not patented, as the male, or pollen, parent. The new *Hydrangea* plant was discovered and selected by the Inventor as a single flowering plant from within the progeny of the stated cross-pollination in a controlled environment in Grand Haven, Mich. during the spring of 2011.

Asexual reproduction of the new *Hydrangea* plant by softwood cuttings in a controlled environment in Grand Haven, Mich. since the spring of 2011 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'SMHPFL'. These characteristics in combination distinguish 'SMHPFL' as a new and distinct *Hydrangea* plant:

1. Upright and somewhat outwardly spreading plant habit.
2. Strong and sturdy stems.
3. Dark green-colored leaves.
4. Large inflorescences with white-colored sterile flowers that become red with development in the autumn.

Plants of the new *Hydrangea* differ from plants of the female parent, 'Pink Lady M2A', in the following characteristics:

1. Plants of the new *Hydrangea* have larger inflorescences than plants of 'Pink Lady M2A'.
2. In the autumn, plants of the new *Hydrangea* have sterile flowers that are red in color whereas plants of 'Pink Lady M2A' have sterile flowers that are dark pink in color.

Plants of the new *Hydrangea* differ from plants of the male parent, 'Pink Lady M2B', in the following characteristics:

1. Plants of the new *Hydrangea* have larger inflorescences than plants of 'Pink Lady M2B'.
2. In the autumn, plants of the new *Hydrangea* have sterile flowers that are red in color whereas plants of 'Pink Lady M2B' have sterile flowers that are dark pink in color.

Plants of the new *Hydrangea* can be compared to plants of *Hydrangea paniculata* 'Pinky Winky', not patented. In side-by-side comparisons, plants of the new *Hydrangea* differed primarily from plants of 'Pinky Winky' in the following characteristics:

1. Plants of the new *Hydrangea* had larger inflorescences than plants of 'Pinky Winky'.

2. In the autumn, plants of the new *Hydrangea* had sterile flowers that were red in color whereas plants of 'Pinky Winky' had sterile flowers that were dark pink in color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'SMHPFL'.

The photograph on the second sheet is a close-up view of a typical flowering plant of 'SMHPFL'.

DETAILED BOTANICAL DESCRIPTION

Plants used for the aforementioned photographs and the following description were grown during the spring and summer in two-gallon containers in an outdoor nursery in Grand Haven, Mich. and under cultural practices typical of commercial *Hydrangea* production. Plants of the new *Hydrangea* were two years old when the photographs and description were taken. In the following description, color references are made to The Royal Horticultural Society Colour Chart, 2001 Edition, except where general terms of ordinary dictionary significance are used.

Botanical description: *Hydrangea paniculata* 'SMHPFL'.

Parentage:

*Female, or seed, parent.*—*Hydrangea paniculata* 'Pink Lady M2A', not patented.

*Male, or pollen, parent.*—*Hydrangea paniculata* 'Pink Lady M2B', not patented.

Propagation:

*Type cutting*.—By softwood cuttings.

*Time to initiate roots, summer*.—About 18 days at temperatures of about 24° C.

*Time to produce a rooted young plant, summer*.—About three months at temperatures of about 24° C.

*Root description*.—Fine and thick; white and brown in color.

*Rooting habit*.—Freely branching; dense.

Plant description:

*Plant form and growth habit*.—Perennial deciduous shrub; upright and somewhat outwardly spreading plant habit; broad inverted triangle; strong and sturdy lateral branches; freely branching habit with about nine lateral branches per plant; vigorous growth habit.

*Plant height*.—About 59 cm.

*Plant diameter or area of spread*.—About 62 cm.

*Lateral branches*.—Length: About 52 cm. Diameter: About 5 mm. Internode length: About 5 cm. Texture: Pubescent. Strength: Strong, sturdy. Color: Close to 177B; with development becoming closer to 200D.

Leaf description:

*Arrangement*.—Opposite, simple.

*Length*.—About 14 cm.

*Width*.—About 7.4 cm.

*Shape*.—Ovate.

*Apex*.—Acuminate.

*Base*.—Obtuse.

*Margin*.—Serrulate.

*Texture, upper and lower surfaces*.—Coarse; pubescent.

*Venation pattern*.—Pinnate.

*Color*.—Developing leaves, upper surface: Close to 143A. Developing leaves, lower surface: Close to 143C. Fully expanded leaves, upper surface: Close to 137A; venation, close to 139A. Fully expanded leaves, lower surface: Close to 137C; venation, close to 145C.

*Petioles*.—Length: About 1 cm. Diameter: About 3 mm. Texture, upper and lower surfaces: Smooth, glabrous. Color, upper surface: Close to 152B. Color, lower surface: Close to 145A.

Flower description:

*Flower type and habit*.—Single sterile and fertile flowers arranged on large terminal conical mophead-type panicles; flowers face upright or outwardly.

*Fragrance*.—None detected.

*Natural flowering season*.—Continuous flowering throughout the summer in Grand Haven, Mich.

*Quantity of flowers*.—Freely flowering habit; about 84 fertile flowers and about 77 sterile flowers per inflorescence.

*Inflorescence height*.—About 14 cm.

*Inflorescence diameter*.—About 15.5 cm.

*Flower diameter, fertile flowers*.—About 8 mm.

*Flower depth (height), fertile flowers*.—About 5 mm.

*Flower diameter, sterile flowers*.—About 5.1 cm.

*Flower depth (height), sterile flowers*.—About 1.7 cm.

*Flower buds, fertile flowers*.—Length: About 6 mm. Diameter: About 3 mm. Shape: Obovate. Color: Close to 155B.

*Flower buds, sterile flowers*.—Length: About 5 mm. Diameter: About 3 mm. Shape: Obovate. Color: Close to 142B.

*Petals, fertile flowers only*.—Arrangement: Six in a single whorl. Length: About 4 mm. Width: About 2 mm. Shape: Ovate. Apex: Acute. Base: Cuneate. Margin: Entire. Texture, upper and lower surfaces: Smooth, glabrous. Color: When opening, upper and lower surfaces: Close to 158C. Fully opened, upper and lower surfaces: Close to 158C.

*Sepals, fertile flowers*.—Quantity per flower: Five in a single whorl. Length: About 4 mm. Width: About 2 mm. Shape: Subulate. Apex: Acute. Base: Cuneate. Margin: Entire. Texture, upper and lower surfaces: Smooth, glabrous. Color: When opening, upper surface: Close to 142D. When opening, lower surface: Close to 142B. Fully opened, upper surface: Close to 142D. Fully opened, lower surface: Close to 142C.

*Sepals, sterile flowers*.—Quantity per flower: Four in a single whorl. Length: About 2.6 cm. Width: About 2.4 cm. Shape: Elliptic. Apex: Obtuse. Base: Obtuse. Margin: Entire. Texture, upper and lower surfaces: Smooth, glabrous. Color: When opening, upper surface: Close to 150C. When opening, lower surface: Close to 150D. Fully opened, upper and lower surfaces: Close to 155A to 155B; in the autumn, color becoming progressively closer to 50C, then closer to 51A and eventually closer to 53B.

*Pedicels, fertile flowers*.—Angle: About 20° to 30° from inflorescence axis. Strength: Strong, sturdy. Length: About 8 mm. Diameter: About 1 mm. Texture: Pubescent. Color: Close to 149D.

*Pedicels, sterile flowers*.—Angle: About 40° to 50° from inflorescence axis. Strength: Strong, sturdy. Length:

About 2 cm. Diameter: About 2 mm. Texture: Pubescent. Color: Close to 157A.

*Reproductive organs, fertile flowers*.—Stamens: Quantity per flower: About eleven. Filament length: About 5 mm. Filament color: Close to 149D. Anther shape: Lobed. Anther length: About 2 mm. Anther color: Close to 87B. Pollen amount: None observed. Pistils: Pistil quantity per flower: About four. Pistil length: About 5 mm. Stigma shape: Oblong. Stigma color: Close to 157C. Style length: About 3 mm. Style color: Close to 157C. Ovary color: Close to 149C.

*Reproductive organs, sterile flowers*.—Stamens: Quantity per flower: About eight. Filament length: About 1 mm. Filament color: Close to 145C. Anther shape: Round. Anther length: About 0.5 mm. Anther color: Close to 166B. Pollen amount: None observed. Pistils: Pistil quantity per flower: One. Pistil length: About 1 mm. Stigma shape: Round. Stigma color: Close to 145C. Style length: About 1 mm. Style color: Close to 145C. Ovary color: Not observed.

*Seeds*.—Seed production has not been observed on plants of the new *Hydrangea*.

Disease & pest resistance: Plants of the new *Hydrangea* have been observed to have resistance to root rot pathogens. Plants of the new *Hydrangea* have not been observed to be resistant to pests and other pathogens common to *Hydrangea* plants.

Temperature tolerance: Plants of the new *Hydrangea* have been shown to be tolerant to temperatures ranging from about −31° C. to about 38° C.

It is claimed:

1. A new and distinct *Hydrangea* plant named 'SMHPFL' as illustrated and described.

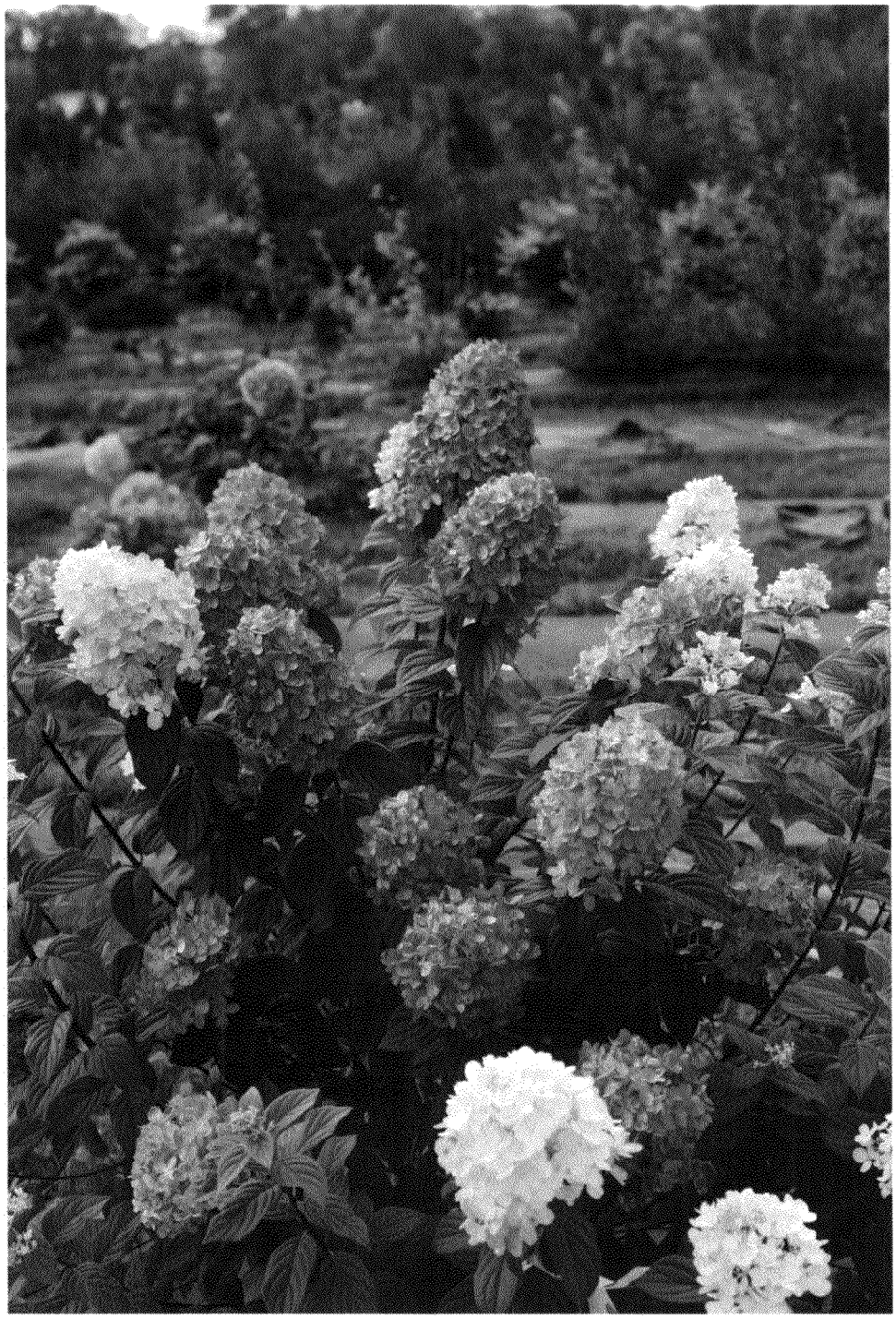

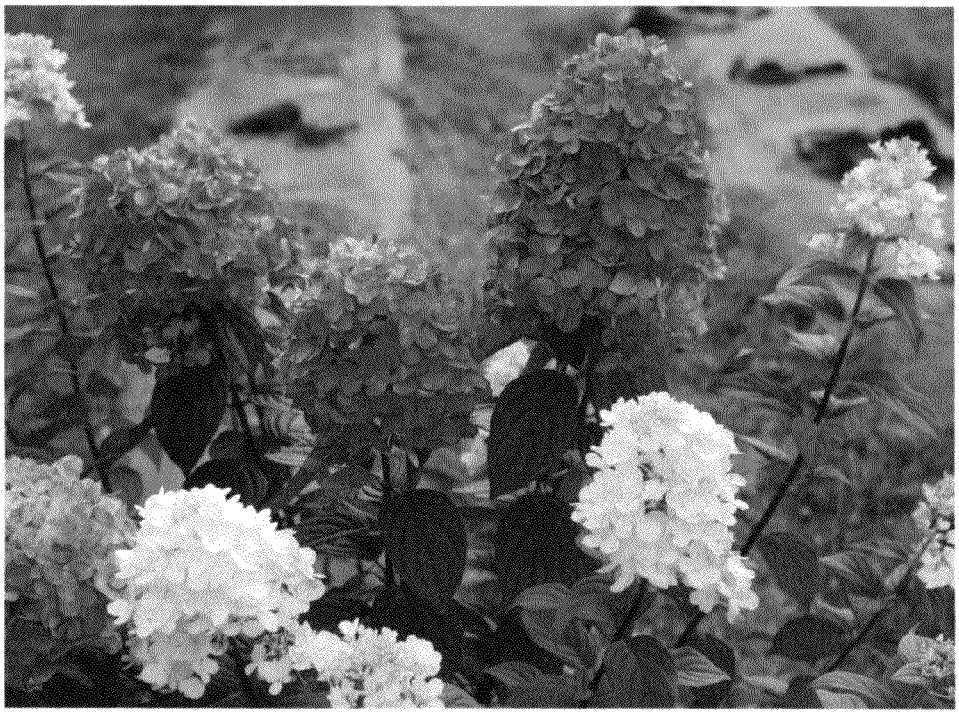

* * * * *